United States Patent [19]

Parziale et al.

[11] Patent Number: 5,310,924
[45] Date of Patent: May 10, 1994

[54] PROCESS FOR PREPARING THIABENDAZOLE

[75] Inventors: Patti A. Parziale; Tzu-Ching Chang; Lynn E. Applegate, all of Wilmington, Del.

[73] Assignee: E. I. Du Pont de Nemours and Company, Wilmington, Del.

[21] Appl. No.: 55,438

[22] Filed: Apr. 30, 1993

[51] Int. Cl.$^5$ .......................................... C07D 417/04
[52] U.S. Cl. ........................................................ 548/181
[58] Field of Search ................................ 548/181, 310.7

[56] References Cited

FOREIGN PATENT DOCUMENTS

| 99787 | 8/1973 | German Democratic Rep. ........................................ 548/181 |
| 127931 | 10/1977 | German Democratic Rep. ........................................ 548/181 |

OTHER PUBLICATIONS

Hofmann, Imidazole pp. 260–267 (1953).
Kutritzky, Comprehensive Heterocyclic Chemistry vol. 5 p. 470 (1984).
Sklyaroua, Zh Org. Khim 22 p. 645 (1986).
Tsuchya, Chem Pharm Bull 35 2985 (1987).

Primary Examiner—Robert Gerstl
Attorney, Agent, or Firm—Charles E. Feeny

[57] ABSTRACT

Process for preparing 2-(4-thiazolyl)-1H-benzimidazole (generic name: thiabendazole) by the acid-catalyzed condensation of o-phenyldiamine and 4-cyanothiazole in solution in water or mixtures of water with miscible co-solvents (solvents which upon mixing with water in all proportions form a homogeneous mixture, as well as, other partially miscible solvents which upon mixing with water in some proportions form a homogeneous mixture under the reaction conditions of the process of this invention).

10 Claims, No Drawings

PROCESS FOR PREPARING THIABENDAZOLE

FIELD OF THE INVENTION

The present invention relates to an improved process for preparing 2-(4-thiazolyl)-1H-benzimidazole (generic name: thiabendazole) by the acid-catalyzed condensation of o-phenyldiamine and 4-cyanothiazole in solution in water or mixtures of water with miscible co-solvents.

BACKGROUND OF THE INVENTION

Thiabendazole gained commercial importance when Brown et al. (J. Am. Chem. Soc. 83, 1764 (1961)) reported that the compound prepared by reacting 4-thiazolecarboxamide with o-phenylenediamine using a polyphosphoric acid catalyst exhibited broad spectrum anthelmintic activity without adverse toxic effects. The reaction described by Brown et al. was conducted at a temperature of 250° C. and resulted in a 64% yield of thiabendazole. Thiabendazole continues to be extensively used for the treatment and/or prevention of helminthiasis in livestock. Thiabendazole is, also, a systemic fungicide widely used for pre-and post-harvest spoilage control of raw agricultural commodities. Because of the commercial importance of thiabendazole, the chemical literature is replete with various other synthetic routes aimed at producing this pharmacologically and fungicidally active compound in high yield and high purity. Prior art processes for preparing thiabendazole suffer from inherent drawbacks and inconveniences, such as low yields, additional purification steps, long reaction times, environmentally undesirable organic solvents and high pressure reaction conditions. Hence, it would be a significant improvement in the art, if thiabendazole could be efficiently prepared under mild conditions in high yield and in the purest possible form for agricultural and pharmaceutical use. It would also be an advantage, if it could be prepared using a simple, one-step, environmentally friendly process which is easily adapted to commercial scale production.

SUMMARY OF THE INVENTION

The process of the present invention overcomes the disadvantages of prior processes by conducting the acid-catalyzed condensation of o-phenylenediamine and 4-cyanothiazole in water or mixtures of water with miscible co-solvents. This process produces thiabendazole in high yield and high purity using a low-cost one-step process. An advantage of the present process is that the reaction is carried out in water, or mixtures of water with miscible co-solvents, in which all components of the reaction mass, except the product thiabendazole, are soluble. Consequently, thiabendazole can be isolated simply by filtering and washing it with water. Hence, it will be appreciated by those skilled in the art that a substantial reduction in the costs associated with disposing of organic solvents is accomplished when the method of this invention is employed to manufacture thiabendazole. Another advantage of this improved process is that, the reaction is carried out under mild conditions, i.e., at nominal atmospheric pressure and reaction temperatures, and within a commercially feasible period of time.

DETAILED DESCRIPTION OF THE INVENTION

The present invention relates to a process for preparing thiabendazole which comprises reacting o-phenylenediamine and 4-cyanothiazole in solution in water, or in solution in mixtures of water with miscible co-solvents, at a temperature in the range between 80° and 145° C. and a pH of from 2.5 to 6.0 for a time sufficient to effect the desired conversion to thiabendazole, and recovering thiabendazole from the reaction mixture.

The acid-catalyzed condensation reaction of this invention is carried out in water or mixtures of water with miscible co-solvents. The term "miscible" as used herein includes solvents which upon mixing with water in all proportions form a homogeneous mixture, as well as, other partially miscible solvents which upon mixing with water in some proportions form a homogeneous mixture under the reaction conditions of the process of this invention. Suitable miscible co-solvents include: alkanols containing 3 to 8 carbon atoms, alkanediols containing 2 to 8 carbon atoms, alkane polyethers containing 4 to 10 carbon atoms and 2 to 4 oxygen oxygen atoms, and alkoxyalkanols having 1 to 8 carbon atoms in the alkoxy group and 1 to 8 carbon atoms in the alkanol portion of the molecule. Exemplary of alcohols are methanol, ethanol, 1-propanol, 2-propanol, 2-methyl-1-propanol (isobutyl alcohol), 1-butanol, 2-butanol, 2-pentanol, and cyclohexanol; of alkanediols: 1,2-ethanediol, 1,2-propane-diol, 1,3-propanediol, and 1,5-pentane-diol; of ethers: 1,4-dioxacyclohexane (dioxane), 1,1'-oxybis-[2-methoxyethane] (diglyme), and 2,5,8,11-tetraoxadodecane (triglyme); of alkoxyalkanols: the Cellosolve type, such as 2-methoxyethanol, and 2-ethoxyethanol. Other suitable co-solvents include aprotic solvents, e.g., N,N-dimethylformamide (DMF), and dimethylsulfoxide (DMSO); and other organic solvents, e.g., N,N-dimethylacetamide (DMAC), and N-methyl-2-pyrrolidone. Preferably, the reaction is carried out in water because it is most economical and provides substantial environmental benefits in the form of reduced wastes.

The reaction will occur at temperatures at 80° C. and above. Below 80° C., the reaction proceeds too slowly to be practical; e.g. below that temperature, the reaction would require at least 24 hours to provide a yield exceeding 85%. Generally the reaction mixture should be maintained between 80° C. and 145° C., preferably at the reflux temperature of the reaction mixture. If desired, the reaction can be carried out at temperatures in excess of such reflux temperatures; however, in that event, pressure reaction equipment may be required. For purposes of efficiency and safety, the reaction is usually carried out at the nominal atmospheric boiling point of the reaction mixture.

If the pH is not maintained in the range between 2.5 and 6.0, the reaction of o-phenylenediamine and 4-cyanothiazole will be very slow or not occur at all. As the reaction proceeds, the pH of the reaction mixture increases, because of ammonia liberated as a by-product of the reaction. Therefore, sufficient acid must be added periodically to the reaction mixture until formation of thiabendazole is determined to be complete. In that way, by-product ammonia generated during the reaction is neutralized, and the reaction mass is maintained at a pH in the range between 2.5 and 6.0 required to ensure complete conversion to thiabendazole within a reasonable period of time. Preferably, the pH is maintained in the range between 3.5 and 4.5. When o-phenylenediamine dihydrochloride is used, the pH of the reaction mixture is increased by adding a base in sufficient proportion to provide a pH level in the range between 2.5 and 6.0, preferably between 3.5 and 4.5.

The concentration of the starting materials (o-phenylenediamine and 4-cyanothiazole) in the reaction mixture can range between:

Broadest: 0.7 moles/l and 5.0 moles/l of reaction mixture;
Preferred: 2.2 moles/l and 4.0 moles/l of reaction mixture.

Above a concentration of 5.0 moles/l, the reaction mixture containing the solid thiabendazole product will be too thick and therefore difficult to stir. Below a concentration of 0.7 moles/l, the reaction proceeds too slowly to be practical. In order to assure an efficient and economic process high concentrations will usually be chosen.

Reaction time depends upon the temperature, pH, and concentration of the reactants. Generally, complete conversion of the reactants to thiabendazole can be completed within time periods ranging between about 1.5 and about 12 hours, usually between 2 and 6 hours.

Suitable mineral acids which can be used to catalyze this reaction include hydrochloric acid and nitric acid, as well as, acid salts, i.e., ammonium chloride. Suitable organic acids include inexpensive, easily accessible acids such as acetic acid, oxalic acid and methanesulfonic acid. The preferred acid catalyst is hydrochloric acid because it is a low cost readily available acid. The only restriction with respect to the acid used is that the acid and the corresponding acid salt of o-phenylenediamine be soluble in the reaction medium.

The mole ratio of o-phenylenediamine to 4-cyanothiazole can range between 1:0.9 and 1:1.1. For economic reasons it is undesirable for one of the reactants to be present in large excess. Therefore, the preferred mole ratio of o-phenylenediamine to 4-cyanothiazole is 1:0.95 to 1:1.05, which allows efficient use of the reactants. These same ratios apply when o-phenylenediamine dihydrochloride is used as a reactant.

The temperature of the reaction medium to which o-phenylenediamine is added can range between about 25° C. up to about 95° C. Since solvents deoxygenate on heating, it will be advantageous if o-phenylenediamine is added to a heated reaction medium with less dissolved oxygen present to react with o-phenylenediamine.

In a preferred embodiment, to a suitable reaction vessel is charged water containing trace amounts of ascorbic acid, an antioxidant, and ethylenediaminetetraacetic acid (EDTA), a metal deactivator. Because o-phenylene-diamine is sensitive to dissolved oxygen in solvents, ascorbic acid which functions as an oxidation inhibitor is added prior to o-phenylenediamine. EDTA, which complexes with metals is also added and prevents metal oxidation of o-phenylenediamine. The system is purged with nitrogen to remove air and a nitrogen blanket is maintained for the duration of the reaction. The aqueous solution is heated using an oil bath, and when the pot temperature reaches 95° C., o-phenylenediamine is added. Since water deoxygenates on heating, o-phenylene-iamine is added to a heated reaction medium with less dissolved oxygen present to react with o-phenylenediamine. Hydrochloric acid is added in a controlled manner to adjust the pH of the reaction mixture to a desired level and the amount used is recorded. An exothermic acid-base reaction occurs and o-phenylenediamine monohydrochloride salt is formed. A stoichiometric amount of 4-cyanothiazole is charged to the reaction vessel. Following addition of 4-cyanothiazole, the reaction mixture is heated to reflux (103°-104° C.). During the reaction, the pH is maintained within +/−0.2 of the desired level by periodic addition of concentrated hydrochloric acid. Since thiabendazole is only slightly soluble in water, the product precipitates as it is formed in the reaction mixture. The reaction is monitored by gas chromatography and determined to be complete when the peaks corresponding to o-phenylenediamine and 4-cyanothiazole are negligible. Upon completion of the reaction, the reaction mass is cooled to 50° C. A sufficient amount of 50° C. deionized water is added to dilute the reaction mass and the solid product is separated from the mother liquor by vacuum filtration. The filtered cake is washed with portions of fresh deionized water until the filtrate gives a negative test for chloride ion using $AgNO_3$ solution which indicates the ammonium chloride coproduct is removed. The solid thiabendazole product is dried in a vacuum oven under 15-20" Hg and at a temperature of 80°-90° C.

The order of addition of the starting materials, o-phenylenediamine followed by 4-cyanothiazole, is not critical, hence a solution of o-phenylenediamine can be acidified at room temperature and then added to a heated reaction vessel containing a solution comprising 4-cyanothiazole and optionally trace amounts of ascorbic acid and EDTA. Following addition of acid, 4-cyanothiazole is added. The manner in which 4-cyanothiazole is added is not critical, hence 4-cyanothiazole can be added all at once or progressively as a solution in methanol or other solvent.

In another embodiment, a stoichiometric amount of 4-cyanothiazole is dissolved in methanol and added dropwise to the 95° C. aqueous reaction mixture. Methanol is distilled out of the reaction vessel during addition.

An alternate technique is inverse addition, wherein an aqueous solution of o-phenylenediamine is adjusted to a desired pH level at room temperature and added in a controlled manner to a 95° C. aqueous solution comprising a stoichiometric amount of 4-cyanothiazole, and trace amounts of ascorbic acid and EDTA.

The o-phenylenediamine can be used in the form of a flaked or granular solid, a melt or in the form of a mineral acid salt, such as o-phenylenediamine dihydrochloride. When o-phenylenediamine dihydrochloride is used, the pH of the reaction mixture will be increased by adding a base in sufficient proportion to provide a pH value in the range between 2.5 and 6.0. An exemplary base which can be employed to adjust the initial pH of the reaction mixture is sodium hydroxide. Other suitable bases are ammonium hydroxide and tertiary amines such as triethylamine. Primary and secondary amines should be avoided because these compounds can react with 4-cyanothiazole.

Although the addition of a trace amount of ascorbic acid, an antioxidant is not essential to the success of this process, ascorbic acid may be added to avoid negligible amounts of colored impurities in the final product. Colored impurities, compounds containing chromophoric groups, may be present when o-phenylenediamine can not be scrupulously restricted from exposure to air, such as in laboratory scale preparations.

The concentration of ascorbic acid in the reaction mixture can range between

Broadest: 0 mole/l and $9 \times 10^{-3}$ mole/l of reaction mixture,
Preferred: $2.5 \times 10^{-3}$ mole/l and $4.5 \times 10^{-3}$ mole/l.

The addition of a trace amount of EDTA, a metal deactivator is optional and may be added to complex trace amounts of metals originating from reagents or equipment used in the process. The concentration of EDTA in the reaction mixture can range between:

Broadest: 0 mole/l and $5.4 \times 10^{-3}$ mole/l,
Preferred: $1.5 \times 10^{-3}$ mole/l and $2.7 \times 10^{-3}$ mole/l.

It is to be understood that the reaction, while described as being conducted in a batchwise mode, may also be conducted in a continuous mode by methods known to those skilled in the art. For example, an acid may be combined with the o-phenylenediamine feed stream before mixing with the 4-cyanothiazole feed stream.

The following examples further illustrate the invention.

EXAMPLE 1

Preparation of Thiabendazole in Water

To a 500 ml four-neck, round-bottom flask fitted with a mechanical stirrer, a condenser, pH probe and thermometer were charged 100 ml of deionized water containing 0.1 g ($3.4 \times 10^{-4}$ mole) ethylenediaminetetraacetic acid (EDTA) and 0.1 g ($5.7 \times 10^{-4}$ mole) ascorbic acid. The reaction vessel was purged with nitrogen and then nitrogen blanketed for the duration of the reaction. The aqueous solution containing EDTA and ascorbic acid was heated using an oil bath. When the solution temperature reached 95° C., 54 grams (0.5 mole) of o-phenylenediamine were charged, followed by dropwise addition of 26 ml concentrated hydrochloric acid (corresponding to 38% hydrogen chloride) to adjust the pH to a value of 3.5. Subsequently, 55 grams (0.5 mole) of 4-cyanothiazole were added to the aqueous solution of o-phenylenediamine monohydrochloride and the mixture was refluxed (103°–104° C.) for 5.5 hours. During this time, the pH was maintained at approximately 3.5 (+/−0.2) by periodic addition of 38% HCl solution. An additional 15.5 ml of 38% HCl solution was added to the reaction mixture during the course of the reaction.

The product, thiabendazole, precipitated as it was formed in the reaction mixture. The reaction was monitored by gas chromatography and determined to be complete when the peaks corresponding to o-phenylenediamine and 4-cyanothiazole were negligible. The reaction mass was allowed to cool to 50° C. and 150 ml of 50° C. deionized water was added to thin the mixture before being vacuum filtered using a medium fritted glass filter. The solid product was washed four times with 300 ml portions of deionized water. The washed precipitate was dried overnight in a vacuum oven under 15–20" Hg and at a temperature of 80°–90° C. A total of 89.77 grams of thiabendazole were obtained which corresponds to an 89.3% yield. The color of dry thiabendazole was cream. High Performance Liquid Chromatography (HPLC) using a Hewlett-Packard Model 1090M showed that the purity was 98.77% (based on % area).

EXAMPLES 2 and 3

The same procedure as that described in Example 1 was carried out with the exception that the concentrated hydrochloric acid was added dropwise in sufficient proportion to adjust the pH to a higher value and the desired pH level was maintained within +/−0.2 for the duration of the reaction. Table 1 demonstrates that excellent yields of thiabendazole were obtained in 2.5 to 5.5 hours for all pH levels. The purity based on HLPC % area increased as the pH decreased.

TABLE 1

| Effect of pH on Yield and Purity of Thiabendazole | | | | | |
|---|---|---|---|---|---|
| pH | Rxn Time (hrs.) | HCl (mole) | Mole Ratio (OPD:HCl) | % Yield | % Purity (HPLC % area) |
| 3.5 | 5.5 | 0.50 | 1:1 | 89.3 | 98.77 |
| 4.0 | 2.5 | 0.48 | 1:0.96 | 88.7 | 98.36 |
| 5.5 | 3.5 | 0.47 | 1:0.94 | 91.1 | 98.06 |
| 4.0$^a$ | 2.5 | 0.50 | 1:1 | 85.1 | 98.53 |

$^a$described in Example 4.

EXAMPLE 4

Preparation of Thiabendazole in Water without Ascorbic Acid and EDTA

The same procedure as that described in Example 1 was carried out at a pH of approximately 4.0 (+/−0.2) in the absence of EDTA and ascorbic acid. A yield of 85.1% was obtained, and HPLC analysis showed that the purity was 98.30% (based on % area).

EXAMPLE 5

Preparation of Thiabendazole in Water with Dropwise Addition of 4-Cyanothiazole Dissolved in Methanol, Which is Distilled Off During Addition To a 500 ml four-neck, round-bottom flask fitted with a mechanical stirrer, condenser, thermometer and pH probe were charged 100 ml of deionized water, 0.1 grams ($3.4 \times 10^{-4}$ mole) of EDTA and 0.1 grams ($5.7 \times 10^{-4}$ mole) ascorbic acid. The reaction vessel was purged with nitrogen and then nitrogen blanketed for the duration of the reaction. The aqueous solution containing EDTA and ascorbic acid was heated using an oil bath. When the solution temperature reached 95° C., 54 grams (0.5 mole) of o-phenylenediamine were charged, followed by, dropwise addition of 16 ml concentrated hydrochloric acid (corresponding to 38% hydrogen chloride) to adjust the pH to a value of 4.0. Subsequently, 55 grams (0.5 mole) of 4-cyanothiazole were dissolved in 100 ml of methanol and added dropwise over 2 hours to the aqueous solution of o-phenylenediamine monohydrochloride. Methanol was distilled out of the reaction vessel via a take off condenser during addition. The reaction mixture was heated to reflux and after 50 min at reflux 50 ml of deionized water was added. The reaction mixture was held at reflux (103°–104° C.) for a period of 3 hours. During this time, the pH was maintained at approximately 4.0 (+/−0.2) by periodic addition of 38% HCl solution. An additional 25.5 ml of 38% HCl solution was added to the reaction mixture during the course of the reaction. The reaction mass was allowed to cool to 50° C. before being vacuum filtered using a medium fritted glass filter. The same procedure as that described in Example 1 was carried out for washing and drying of thiabendazole.

A total of 92.20 grams of thiabendazole were obtained which corresponds to a 91.7% yield. HPLC analysis showed that the purity was 98.80% (based on % area).

EXAMPLES 6–8

The same procedure as that described in Example 5 was carried out with the exception that the concentrated hydrochloric acid was added dropwise in sufficient proportion to adjust the pH to a desired level which was maintained within +/−0.2 for the duration of the reaction. Table 2 demonstrates that the percent yield of thiabendazole is directly related to pH, i.e., the lower the pH the lower the yield. At a pH of 3.0 only a 60.7% yield was obtained even after 7 hours.

TABLE 2

Effect of pH on Yield and Purity of Thiabendazole Using Addition of 4-Cyanothiazole in Methanol

| pH | Rxn Time (hrs.) | % Yield | % Purity (HPLC area %) |
|---|---|---|---|
| 4.5 | 3.0 | 93.0 | 98.37 |
| 4.0 | 3.0 | 91.7 | 98.80 |
| 3.5 | 3.0 | 84.2 | 99.58 |
| 3.0 | 7.0 | 60.7 | 99.61 |

EXAMPLE 9

Preparation of Thiabendazole in Water Using Inverse Addition

The same procedure as that described in Example 1 was carried out with the exception that 54 grams (0.5 mole) of o-phenylenediamine were dissolved in 100 ml of deionized water and adjusted to a pH of 4.0 at room temperature using 28 ml of concentrated hydrochloric acid (corresponding to 38% hydrogen chloride). The resulting solution was added dropwise over 2 hours to the reaction vessel containing a solution at 95° C. comprising 100 ml of deionized water, 0.1 gram (3.4×10−4 mole) of EDTA, 0.1 gram (5.7×10−4 mole) of ascorbic acid and 55 grams (0.5 mole) of 4-cyanothiazole. Following this, the reaction mixture was refluxed (103°–104° C.) for 7 hours. During this time the reaction mixture was maintained at a pH of approximately 4.0 (+/−0.2) by addition of 38% HCl solution. An additional 13.5 ml of 38% HCl solution was added to the reaction mixture during the course of the reaction. The same procedure as that described in Example 5 was carried out for filtration, washing and drying of thiabendazole.

A total of 93.22 grams of thiabendazole were obtained which corresponds to a 92.7% yield. HPLC analysis showed that the purity was 98.64% (based on % area).

EXAMPLES 10–13

Preparation of Thiabendazole in Water at pH 4.0 in which the Reaction Time Is Varied A series of reactions were carried out at a pH of approximately 4.0 (+/−0.2) using the same procedure described in Example 1. The results listed in Table 3 demonstrate that the reaction time does not significantly effect the purity of thiabendazole. For experiments which used 38% HCl solution for pH adjustment, the color of the solid thiabendazole varied from tan, to light tan to cream for the 4.0, 2.5 and 1.5 hour runs, respectively.

There was not a significant difference in the purity of the solid thiabendazole obtained when the pH was adusted with 19% HCl solution. In this case, the color of the solid thiabendazole was light tan.

TABLE 3

Effect of Reaction Time and Concentration of HCl on Yield and Purity of Thiabendazole

| Ex. # | Rxn Time (hrs.) | HCl (% Conc.) | % Yield | % Purity (HPLC % area) |
|---|---|---|---|---|
| 10 | 4.0 | 38 | 90.1 | 98.57 |
| 11 | 2.5 | 38 | 91.6 | 98.84 |
| 12 | 1.5 | 38 | 81.2 | 98.60 |
| 13 | 2.5 | 19 | 86.2 | 98.53 |

EXAMPLE 14

Preparation of Thiabendazole in Water Using O-phenylenediamine Dihydrochloride

To a 1 liter four-neck flask equipped with a mechanical stirrer, a condenser, pH probe and thermometer were added 54 grams (0.5 mole) of 4-cyanothiazole, 90.5 grams (0.5 mole) of o-phenylenediamine dihydrochloride and 250 ml of deionized water. Sodium hydroxide pellets were added in sufficient proportion to increase the pH of the reaction mixture to a value of 4.0. The mixture was heated to reflux and held at reflux (100°–102° C.) for 4 hours. The reaction was determined to be complete when the peaks corresponding to o-phenylenediamine and 4-cyanothiazole were absent from the gas chromatogram. The reaction mass was allowed to cool to room temperature before adding 0.1N NaOH to adjust the pH to a value within a range of 8–10. The product was filtered, washed three times with 300 ml portions of deionized water, and then dried overnight in a vacuum oven. A total of 78.0 grams of thiabendazole were obtained which corresponds to a 77.5% yield.

EXAMPLES 15–21

Preparation of thiabendazole in Mixtures of Water with Miscible Co-Solvents

The same procedure as that described in Example 1 was carried out with the exception that the reaction medium employed comprised a mixture of water with a miscible co-solvent. The temperature of the reaction mass at reflux was 99°–105° C. for the water-DMF, DMAC and 1-butanol reaction media. For the 50% methanol 50% water system, the pH was adjusted at room temperature and 4-cyanothiazole dissolved in methanol was added dropwise to the 70° C. reaction solution which was then refluxed at 84° C. The isolated product was washed four times with 200 ml portions of 50% methanol 50% water mixture. In all cases, the same mother liquor composition was used to thin the reaction mixture prior to filtering. The results are listed in Table 4.

TABLE 4

Synthesis of Thiabendazole In Aqueous + Organic Media

| Ex. # | Solvent/% | pH | Rxn Time (hrs) | % Yield | % Purity (HPLC % area) |
|---|---|---|---|---|---|
| 15 | Ethanol/50 | 4.0 | 11.0 | 74.1 | 99.47 |
| 16 | DMAC/25 | 4.0 | 2.5 | 84.2 | 99.21 |
| 17 | DMAC/60 | 5.3 | 3.5 | 82.7 | 99.16 |
| 18 | DMF/25 | 4.0 | 2.5 | 83.2 | 99.04 |
| 19 | 1-Butanol/25 | 4.0 | 3.2 | 86.9 | 98.12 |
| 20 | 1-Butanol/25 | 4.5 | 3.2 | 86.9 | 98.08 |
| 21 | 1-Butanol/25 | 3.5 | 3.2 | 84.4 | 99.18 |

As confirmed via HPLC analysis the thiabendazole product prepared using the method disclosed herein is of high purity. Optionally, thiabendazole may be further purified using conventional methods, i.e., organic solvent extraction, recrystallization, and treatment with activated carbon.

The following extraction procedure is one method demonstrated in the laboratory which resulted in an increase in the purity of thiabendazole.

A portion of the thiabendazole product was purified by placing 5 grams in a 125 ml Erlenmeyer flask. To the flask were added 50 ml of water+organic solvent or 100% organic solvent and the mixture was stirred for one hour at a specified temperature. The thiabendazole crystals were filtered at room temperature, washed twice with 50 ml portions of deionized water, and dried in a vacuum oven under 15-20" Hg and at a temperature of 80°-90° C. Table 5 provides the results as determined by HPLC analysis.

TABLE 5

Effect of Organic/Water Solvent Extraction on Purity of Thiabendazole

| Ex. # | % Solvent | % H$_2$O | Temp (°C.) | % Purity (HPLC % area) |
|---|---|---|---|---|
| 5 | (as synthesized) (Solvent: Acetone) | | | 98.80 |
| | 50 | 50 | 56 | 99.28 |
| | 100 | 0 | 53 | 99.33 |
| 12 | (as synthesized) (Solvent: Methanol) | | | 98.60 |
| | 75 | 25 | 60 | 99.32 |
| | 100 | 0 | 60 | 99.50 |
| 13 | (as synthesized) (Solvent: Ethanol) | | | 98.53 |
| | 75 | 25 | 25 | 99.32 |
| | 100 | 0 | 75 | 99.31 |
| 11[b] | (as synthesized) (Solvent: DMAC) | | | 98.68 |
| | 25 (Solvent: DMF) | 75 | RT[c] | 98.91 |
| | 25 (Solvent: 1-Butanol) | 75 | RT | 99.20 |
| | 10 | 90 | RT | 98.98 |

[b]Same procedure as Example 11, but using twice the amount of ascorbic acid and EDTA.
[c]Room temperature.

We claim:

1. A process for preparing thiabendazole which comprises reacting 4-cyanothiazole with (a) o-phenylenediamine in the presence of an acid catalyst, or (b) a protonic acid salt of o-phenylenediamine, at a temperature in the range between 80° and 145° C. and a pH of from 2.5 to 6.0 in solution in water, or in solution in mixtures of water with miscible co-solvents, for a time sufficient to effect the desired conversion to thiabendazole, and recovering thiabendazole from the reaction mass.

2. The process of claim 1 wherein said temperature is from 80° C. up to the reflux temperature of the reaction mixture.

3. The process of claim 1 wherein the mole ratio of o-phenylenediamine to 4-cyanothiazole ranges between 1:0.9 and 1:1.1.

4. The process of claim 1 wherein the miscible co-solvent is methanol, ethanol, 1-propanol, 2-propanol, 2-methyl-1-propanol, 1-butanol, 2-butanol, 2-pentanol, cyclohexanol, 1,2-ethanediol, 1,2-propanediol, 1,3-propanediol, 1,5-pentanediol, 2,5,8,11-tetraoxadodecane, 1,1'-oxybis[2-methoxyethane], 1,4-dioxacyclohexane, 2-methoxyethanol, 2-ethoxyethanol, N,N-dimethylformamide, dimethylsulfoxide, N,N-dimethylacetamide or N-methyl-2-pyrrolidone.

5. The process of claim 1 wherein said acid catalyst is hydrochloric acid, hydrobromic acid, ammonium chloride, ammonium bromide, ammonium acetate, ammonium phosphate, ammonium nitrate, sulfamic acid, zinc chloride, stannous chloride, aluminum chloride, acetic acid, oxalic acid, propionic acid, adipic acid, methanesulfonic acid, benzenesulfonic acid, or p-toluenesulfonic acid.

6. A process for preparing thiabendazole which comprises reacting o-phenylenediamine and 4-cyanothiazole at elevated temperatures in the presence of water or mixtures of water with miscible co-solvents and sufficient hydrochloric acid to maintain a pH of from approximately 2.5 to approximately 6.0, for a time sufficient to effect the desired conversion to thiabendazole, and recovering thiabendazole from the reaction mixture.

7. The process of claim 6 at a temperature from 80° up to the reflux temperature of the reaction mixture.

8. The process of claim 6 wherein the mole ratio of o-phenylenediamine to 4-cyanothiazole ranges between 1:0.9 and 1:1.1.

9. The process of claim 6 wherein the miscible co-solvent is methanol, ethanol, 1-propanol, 2-propanol, 2-methyl-1-propanol, 1-butanol, 2-butanol, 2-pentanol, cyclohexanol, 1,2-ethanediol, 1,2-propanediol, 1,3-propanediol, 1,5-pentanediol, 2,5,8,11-tetraoxadodecane, 1,1'-oxybis[2-methoxyethane], 1,4-dioxacyclohexane, 2-methoxyethanol, 2-ethoxyethanol, N,N-dimethylformamide, dimethylsulfoxide, N,N-dimethylacetamide or N-methyl-2-pyrrolidone.

10. The process of claim 6 wherein said acid catalyst is hydrochloric acid, hydrobromic acid, ammonium chloride, ammonium bromide, ammonium acetate, ammonium phosphate, ammonium nitrate, sulfamic acid, zinc chloride, stannous chloride, aluminum chloride, acetic acid, oxalic acid, propionic acid, adipic acid, methanesulfonic acid, benzenesulfonic acid, or p-toluenesulfonic acid.

* * * * *